United States Patent [19]
Noziri

[11] Patent Number: 5,123,411
[45] Date of Patent: Jun. 23, 1992

[54] COLD COMPRESS ARRANGEMENT

[76] Inventor: Izumi Noziri, 18-13, Kitakarasuyama 7-chome, Setagaya-ku, Tokyo 157, Japan

[21] Appl. No.: 672,774

[22] Filed: Mar. 20, 1991

Related U.S. Application Data

[63] Continuation-in-part of Ser. No. 317,974, Mar. 2, 1989, abandoned.

[30] Foreign Application Priority Data

Mar. 3, 1988 [JP] Japan .................. 63-50443

[51] Int. Cl.$^5$ .................................................. A61F 7/00
[52] U.S. Cl. .................................................. 128/403; 62/4
[58] Field of Search .................. 128/399–403, 128/379, 380, 82.1, 24.1; 62/530, 4

[56] References Cited

U.S. PATENT DOCUMENTS

| | | | |
|---|---|---|---|
| 2,907,173 | 10/1959 | Robbins | 62/4 |
| 3,834,396 | 9/1974 | Foster et al. | 128/403 |
| 3,867,939 | 2/1975 | Moore et al. | 128/400 |
| 3,929,131 | 12/1975 | Hardwick | 128/403 |
| 3,950,158 | 4/1976 | Gossett | 128/403 |
| 4,011,945 | 3/1977 | Bourne et al. | 128/403 |
| 4,114,620 | 9/1978 | Moore et al. | 128/400 |
| 4,427,010 | 1/1984 | Marx | 128/399 |
| 4,576,169 | 3/1986 | Williams | 128/403 |
| 4,641,655 | 2/1987 | Abt | 128/403 |
| 4,671,267 | 6/1987 | Stout | 128/380 |
| 4,846,176 | 7/1989 | Golden | 128/400 |

*Primary Examiner*—William H. Grieb
*Assistant Examiner*—Mark S. Graham
*Attorney, Agent, or Firm*—Wenderoth, Lind & Ponack

[57] ABSTRACT

A cold compress includes a generally flat self-contained cooling member adapted to undergo an endothermic reaction upon physical manipulation. A generally thermal.wetting member which includes a liquid is provided in thermal contact with the self-contained cooling member. An envelopment is provided for sealingly enclosing at least the wetting member including the liquid. The self-contained cooling member includes a substances which undergoes an endothermic reaction upon physical manipulation, whereby heat is absorbed from the wetting member into the self-contained cooling member.

6 Claims, 1 Drawing Sheet

COLD COMPRESS ARRANGEMENT

This application is a continuation-in-part of now abandoned application Ser. No. 07/317,974 filed on Mar. 2, 1989.

BACKGROUND OF THE INVENTION

1. Field of the Invention

This invention relates generally to a cold compress, and more particularly, to a cold compress which is convenient to use and which exhibits an excellent cold compress effect.

2. Description of the Prior Art

The cold compress is extensively used in medical treatments and health maintenance programs, and is usually made up by dipping a towel in cold water and thereafter applying the dampened towel to an injured part of a body.

However, such a cold compress has a short time duration in which the cold compress effect is maintained and is troublesome in that considerable time is required for its operation. Additionally, the cooled towel is low in portability, restricting the place and time it may be used, thus making it difficult to meet emergency requirements. Additionally, the towel after being dipped in cold water may be stored at a predetermined temperature in a refrigerator. However, this not only requires considerable storing and maintenance costs, but it is also low in portability, thus restricting the place and time it may be used.

SUMMARY OF THE INVENTION

An object of present invention is to provide an improved cold compress arrangement having a high portability, to meet emergency requirements so that there is no restriction in the place and time it may be used, which is easy to maintain and low in cost.

According to the present invention, the cold compress arrangement includes a cooling member which enters a low temperature condition for a predetermined time so as to absorb heat. A wetting member containing liquid is provided in contact with the cooling member. At least one of the cooling member and the wetting member is sealingly enclosed in an envelopment.

The cold compress arrangement can be used by taking the cooling member and/or wetting member out of the envelopment and thereafter applying the arrangement in contact with the injury. The cold compress is easy to use, and little time is required for its operation, and the troublesome procedure of dipping a towel in a cold water or the like is not required. Additionally, by virtue of the cooling member, the cooling effect to the wetting member can be maintained for a long time and therefore the cold compress treatment can be effected using a single cold compress arrangement. This not only facilitates use of the cold compress but also effectively improves the cold compress effect, while also lowering cost for maintenance of the cold compress treatment. The cold compress arrangement of this invention is portable in that it is not restricted to a place and time of use. Accordingly, it can meet emergency cold compress treatment requirements.

BRIEF DESCRIPTION OF THE DRAWINGS

Other objects and features of the improved cold compress arrangement according to the present invention will become more apparent from the following description with the accompanying drawings in which like reference numerals and characters designate corresponding parts and elements, in which.

DETAILED DESCRIPTION OF THE INVENTION

Figure 1:
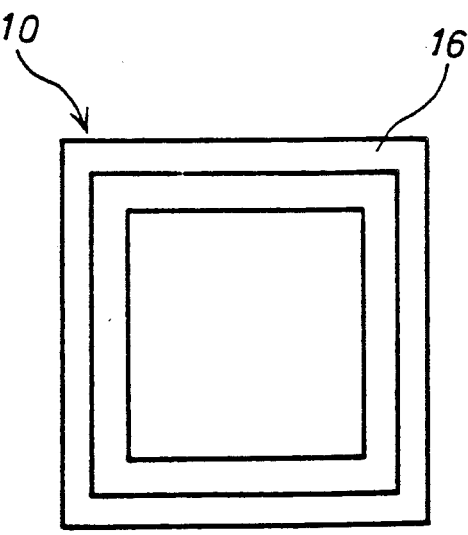
FIG. 1 is a plan view of a first embodiment of a cold compress arrangement in accordance with the present invention.
Figure 2:
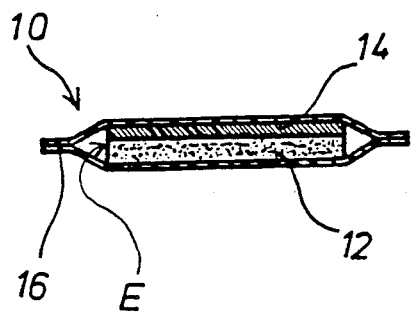
FIG. 2 is a vertical sectional view of the cold compress arrangement of FIG. 1.

Referring now to FIGS. 1 and 2 of the drawings, a first embodiment of a cold compress arrangement is illustrated by the reference numeral 10. The cold compress arrangement 10 includes a cooling member 12 which is adapted upon passing of an electric current or upon some other stimulation, to enter a relatively low temperature condition for a predetermined time. A wetting member 14 is disposed on the thicker cooling member 12 and contains therein liquid, such as water or medicative liquid. The cooling member 12 and the wetting member 14 constitute a cold compress element E and are enclosed within a bag or envelopment 16 in a sealed manner.

The cooling member 12 is known per se and lowers in temperature to a predetermined level, by being rubbed or by some other physical stimulation, thereby absorbing heat for a predetermined time. The wetting member 14 is formed of cloth or fabric, such as non-woven fabric, and has a predetermined level of water content in a liquid state. The cooling member 12 and the wetting member 14 are bonded to each other by an adhesive, thereby forming the cold compress element E. The envelopment 16 is formed of a plastic sheet or film, such as polyethylene film, and is formed into a bag shape. In production, the envelopment 16 is sealed closed at an open mouth section, for example, at an end portion thereof, by thermal bonding or adhesion after the cooling member 12 and the wetting member 14 are enclosed therein. An example of the cooling member 12 is one (trade name: "HIEBO") produced and sold by Johnson Trading Co., Ltd. Of No. 699, Kokufuhongo Oiso-cho, Kanagawa Prefecture, Japan. It will be understood that many other cooling members similar to the above-mentioned cooling member are now extensively on the market.

The manner of usage of the thus fabricated cold compress arrangement 10 will be discussed hereinafter.

The cold compress element E of the arrangement 10 exhibits a cold compress effect by cooling of the wetting member 14 upon physical manipulation of the cooling member 12. More specifically, the envelopment 16 of the cold compress arrangement is first opened by being cut with scissors or the like. Next, the cold compress element E of the cooling member 12 and the wetting member 14 is taken out of the envelopment 16 and is struck in some manner such that physical shock of the cooling member 12 takes place. As a result, the cooling member 12 absorbs heat, thereby cooling the wetting member 14, thus exhibiting the desired cold compress effect.

Upon applying the thus functioning cold compress element E to the injury, a cold compress treatment is effected to the injury at a predetermined temperature and for a predetermined time. In order to interrupt the usage of the cold compress element E during cooling by the cooling member 12 as occasion demands, the cold compress element E of the cooling member 12 and the wetting member 14 is put back into the envelopment 16 and thereafter the envelopment 16 is again sealed. Thus, the cold compress arrangement 10 can be repeatedly used several times if necessary.

Figure 3:
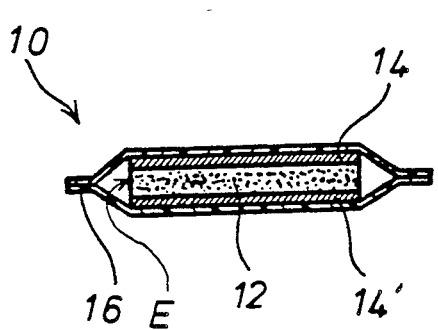
FIG. 3 is a vertical sectional view similar to FIG. 2 but showing a second embodiment of the cold compress arrangement according to the present invention.

FIG. 3 illustrates a second embodiment of the cold compress arrangement in accordance with the present invention, which is similar to the first embodiment with the exception of a further wetting member 14' provided in contact with the thicker cooling member 12. The wetting member 14' is of the same material as the wetting member 14 and therefore functions like the wetting member 14. In this embodiment, the wetting members 14, 14' are respectively bonded to the front and back opposing sides of the cooling member 12 with an adhesive so that the cooling member 12 is interposed between the wetting members 14, 14' to form a one-piece cold compress element E. The thus formed cold compress element E is sealingly enclosed within the envelopment 16 to constitute the cold compress arrangement 10.

This cold compress arrangement 10 can be used to effect a cold compress treatment simultaneously of two injuries in which the right and back sides of the above-mentioned cold compress element E are simultaneously made to contact the two injuries, for example, in case where the cold compress element E is applied under the armpit. Otherwise, the cold compress element E may be used for about twice the time as in the arrangement of FIGS. 1 and 2 by turning over the cold compress element E in the case where a longer cold compress treatment is necessary. Thus, the front side and the back side of the cold compress element E can be used, thereby increasing the range of usage of the cold compress arrangement 10.

Figure 4:
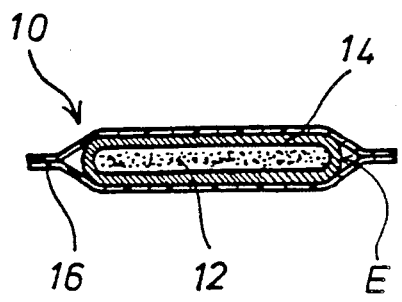
FIG. 4 is vertical sectional view similar to FIG. 2 but showing a third embodiment of the cold compress arrangement according to the present invention.

FIG. 4 illustrates a third embodiment of the cold compress arrangement 10 in accordance with the present invention, which is similar to the above discussed embodiment shown in FIG. 3 except for the configuration of the wetting member 14. In this embodiment, the cooling member 12 is enclosed within the wetting member 14 to form the cold compress element E. The cold compress element E is sealingly enclosed within the envelopment to thereby constitute the cold compress arrangement 10.

The cold compress arrangement 10 of this embodiment is similarly advantageous to the second embodiment, in that the front and back sides of the cold compress element E can be used for simultaneous treatment, for example, in the case where the cold compress element E is applied under the armpit, or in the case where the treatment time may be doubled by turning over the cold compress element E, to thereby use both sides of the cold compress element E. This not only increases the range of usage of the cold compress arrangement 10 but also omits troublesome operations of bonding the cooling member 12 and the wetting member 14 during production of the cold compress element E or after the cold compress element E is taken out of the envelopment 16.

While the cooling member 12 and the wetting member 14 have been shown and described as being enclosed in the same envelopment 16, it will be understood that they may be respectively disposed in separate envelopments, thereby further enhancing the cooling function of the cooling member 12 and the wetting function of the wetting member 14. Additionally, it will be understood that only the wetting member 14 may be enclosed in the envelopment 16.

Although the wetting member 14 has been shown and described as being formed of cloth, such as non-woven fabric, it will be understood that it may be formed of a material which is excellent in water absorbing ability and water holding ability, such as the so-called water-absorptive resin, for the purpose of improving the cold compress effect. In this case, in the use of the cold compress arrangement, the wetting member 14 may be dipped in a liquid, such as cold water, to absorb the liquid before and during usage, thereby further improving the water holding ability and therefore the cold compress effect. Although the wetting member 14 has been shown and described as being enclosed in the envelopment 16 upon absorbing liquid, it will be appreciated that it may not necessarily be enclosed in the envelopment 16 in case where the wetting member 14 is used just after absorbing a liquid upon being dipped in the liquid. This makes it possible to enclose only the cooling member 12 in the envelopment 16 or to otherwise omit the envelopment 16 altogether for both the cooling member 12 and the wetting member 14, thereby lowering the cost of the cold compress arrangement 10. Additionally, the wetting member 14 may be formed of paper or other material which is high in water absorbing ability and water holding ability, thereby further lowering the cost, while increasing the range of usage of the cold compress arrangement 10.

While the cooling member 12 and the wetting member 14 have been shown and described as being previously bonded to each other by an adhesive or the like, it will be understood that covering papers (or so-called peeled-off papers) may be applied to the bonding surfaces of the cooling and wetting members 12, 14 after the adhesive is coated on the bonding surfaces, in which the papers are peeled off to bond the cooling and wetting members 12, 14 during usage of the cold compress arrangement 10. This is suitable in the case where the cooling member 12 and the wetting member 14 are enclosed respectively in separate envelopments and in the case where only the wetting member 14 is enclosed in an envelopment. Additionally, the surface (opposite to the bonding surface) of the wetting member 14 may be coated with an adhesive and covered with the covering paper, in which the wetting member 14 is secured to the injury by the adhesive upon peeling off the covering paper, thereby facilitating fixation of the cold compress element E. Only a part of the bonding surface of the cooling member 12 and the wetting member 14 may be bonded without bonding the whole of the bonding surface, thereby saving adhesive costs of the cold compress arrangement 10.

Although the cooling member 12 has been shown and described as being enclosed with the wetting member 14 in connection with FIG. 4, it will be understood that the wetting member 14 may be enclosed with the cooling member 12, thereby increasing the range of usage of the cold compress arrangement 10. The cooling member 12 may be adapted to absorb heat under another physical stimulus, such as evaporation, or formed of a known low temperature maintaining material. Additionally, the cooling member 12 may be adapted to absorb heat under combination of a chemical stimulus and a physical stimulus. These can further lower the cooling temperature and prolong the cooling time while facilitating adjustment of such temperature and treatment time. The liquid contained in the wetting member 14 may be a medicative liquid or water which is relatively low in temperature in accordance with the purpose of usage.

The surface of the wetting member 14 can be subjected to treatment, such as coating of a medicative material, in order to further improve the cold compress effect.

It will be appreciated that the cold compress arrangement 10 may be used as a medical treatment, in the place of a cooling towel for makeup purpose, and in the place of other cooling devices, such as an ice bag, for generally cooling a part of a human body.

What is claimed is:

1. A cold compress for providing a moisturizing cold compress treatment to skin comprising:
    a self-contained cooling member adapted to undergo an endothermic reaction upon stimulation;
    a wetting member including a liquid, said wetting member being thermally coupled to said self-contained cooling member, said wetting member including a base member formed of fibrous material, said liquid retained in said base member, said wetting member having a thickness smaller than that of said cooling member;
    an adhesive between said self-contained cooling member and said wetting member to bond said cooling member and said wetting member; and
    envelope means for sealingly enclosing therein said self-contained cooling member and said wetting member which are bonded with each other, said envelopment means including a bag-shaped member formed of a plastic film to provide an air impermeable seal;
    wherein said wetting member is adapted for direct contact with the skin upon opening of said envelop means to effect the moisturizing cold compress treatment of the skin.

2. A cold compress as recited in claim 1, wherein said self-contained cooling member comprises a substance which undergoes an endothermic reaction upon stimulation by physical manipulation of said self-contained cooling member, whereby heat is absorbed from said wetting member into said self-contained cooling member.

3. A cold compress as recited in claim 1, said liquid of said wetting member being a medicative liquid, and said wetting member being formed of a non-woven fabric.

4. A cold compress as recited in claim 1, said self-contained cooling member and said wetting member each being generally flat, wherein a first flat surface of said self-contained cooling member is disposed along a flat surface of said wetting member.

5. A cold compress as recited in claim 2, said self-contained cooling member and said wetting member each being generally flat, wherein a first flat surface of said self-contained cooling member is disposed along a flat surface of said wetting member.

6. A cold compress as recited in claim 4, further comprising a second wetting member including a liquid and being generally flat, wherein a second flat surface, opposing the first flat surface, of said self-contained cooling member is disposed along a flat surface of said second wetting member.

* * * * *